(12) United States Patent
Wang et al.

(10) Patent No.: US 9,084,746 B2
(45) Date of Patent: Jul. 21, 2015

(54) THERAPEUTIC APPLICATIONS OF SMAD7

(75) Inventors: Xiao-Jing Wang, Greenwood Village, CO (US); Yosef Rafaeli, Denver, CO (US); Qinghong Zhang, Englewood, CO (US)

(73) Assignee: THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 0 days.

(21) Appl. No.: 13/822,173

(22) PCT Filed: Sep. 21, 2011

(86) PCT No.: PCT/US2011/052499
§ 371 (c)(1),
(2), (4) Date: May 28, 2013

(87) PCT Pub. No.: WO2012/040295
PCT Pub. Date: Mar. 29, 2012

(65) Prior Publication Data
US 2013/0267456 A1    Oct. 10, 2013

Related U.S. Application Data

(60) Provisional application No. 61/385,445, filed on Sep. 22, 2010.

(51) Int. Cl.
*A61K 38/00* (2006.01)
*A61K 45/06* (2006.01)
*A61K 31/7088* (2006.01)
*A61K 38/17* (2006.01)

(52) U.S. Cl.
CPC ............. *A61K 38/00* (2013.01); *A61K 31/7088* (2013.01); *A61K 38/1709* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,684,611 A | 8/1987 | Schilperoort et al. |
| 4,879,236 A | 11/1989 | Smith et al. |
| 4,952,500 A | 8/1990 | Finnerty et al. |
| 5,302,523 A | 4/1994 | Coffee et al. |
| 5,322,783 A | 6/1994 | Tomes et al. |
| 5,384,253 A | 1/1995 | Krzyzek et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,580,859 A | 12/1996 | Felgner et al. |
| 5,589,466 A | 12/1996 | Felgner et al. |
| 5,610,042 A | 3/1997 | Chang et al. |
| 5,656,610 A | 8/1997 | Shuler et al. |
| 5,670,488 A | 9/1997 | Gregory et al. |
| 5,702,932 A | 12/1997 | Hoy et al. |
| 5,736,524 A | 4/1998 | Content et al. |
| 5,780,448 A | 7/1998 | Davis |
| 5,789,215 A | 8/1998 | Berns et al. |
| 5,871,986 A | 2/1999 | Boyce |
| 5,945,100 A | 8/1999 | Fick |
| 5,981,274 A | 11/1999 | Tyrrell et al. |
| 5,994,624 A | 11/1999 | Trolinder et al. |
| 6,605,443 B1 | 8/2003 | Nakao et al. |
| 2007/0178439 A1 | 8/2007 | Smith et al. |
| 2007/0231401 A1 | 10/2007 | Tseng et al. |
| 2009/0155193 A1 | 6/2009 | Joabsson et al. |

FOREIGN PATENT DOCUMENTS

| | | |
|---|---|---|
| CN | 101316602 | 12/2006 |
| WO | WO-94/09699 | 5/1994 |
| WO | WO-95/06128 | 3/1995 |
| WO | WO-99/50296 | 10/1999 |
| WO | WO-03/006057 | 1/2003 |
| WO | WO-2007038686 | 4/2007 |

OTHER PUBLICATIONS

Liu et al. Acta Academiae Medicinae Militaris Tertiae. 30(23);2198-2202:2008.*
Liu et al. Acta Academiae Medicinae Militaris Tertiae. 2008.*
Liu et al. Acta Academiae Medicinae Militaris Tertiae. 2008. (Translation).*
Elmotasem. J Pharm Sci. 2008, 3 (1):12-29.*
Aragon, et al., "Structural Basis for the Versatile Interactions of Smad7 with Regulator WW Domains in TGF-beta Pathways", Structure, (2012), vol. 20, pp. 1726-1736.
Caron, et al., "Endosome disruption enhances the functional nuclear delivery of Tat-fusion proteins", Biochem Biophys Res Comm, (2004), vol. 319, pp, 12-20.
Hariharan, et el., "Structure-function relationship of inhibitory Smads: Structural flexibility contributes to functional divergence", Proteins, (2008), vol. 71, pp. 1853-1862.
Liu, B. et al., "Expression of TAT-Smad7-HA fusion protein and validation of its transduction activity", Journal of Third Military Medical University (2008), vol. 30, pp. 2198-2202, 9 pages English translation from Chinese.
Brooks, H. "Tat peptide-mediated cellular delivery: back to basics," Advanced Drug Delivery Reviews, vol. 57, Issue 4, Feb. 2005, pp. 559-577.
Cawley, M. and Benson, L., "Current Trends in Managing Oral Mucositis," Clin. Journ. of Onocology Nursing, Oct. 2005, vol. 9, No. 5, pp. 584-592.

(Continued)

*Primary Examiner* — Amber D Steele
*Assistant Examiner* — Schuyler Milton
(74) *Attorney, Agent, or Firm* — Foley & Lardner LLP

(57) ABSTRACT

The invention provides methods and compositions for the treatment of inflammatory and/or tissue damage conditions. In particular, the use of Smad7 compositions delivered locally or systemically to a site of inflammation and/or tissue damage is described. Other specific embodiments concern treatment or prevention of side effects caused by radiation and/or chemotherapy, including but not limited to mucositis.

20 Claims, 8 Drawing Sheets

(56) References Cited

OTHER PUBLICATIONS

Cardarelli, F., et al., "Tuning the Transport Properties of HIV-1 Tat Arginine-Rich Motif in Living Cells," Traffic, Apr. 2008, vol. 9, Issue 4, pp. 528-539.

Chen C., and Okayama, H., "High-efficiency transformation of mammalian cells by plasmid DNA," Mol Cell Biol. Aug. 1987; 7(8): 2745-2752.

Fechheimer, M., et al., "Transfection of mammalian cells with plasmit DNA by scrape loading and sonication loading," Dec. 1987, Proc. Natl. Acad. Sci, vol. 84, pp. 8463-8467.

First Office Action received in Chinese Appln. No. 201180051033.3 dated Jun. 27, 2014. (English Translation Not Provided).

Fischer, P.M., "Cellular Uptake Mechanisms and Potential Therapeutic Utiltiy of Peptidic Cell Delivery Vectors: Progress 2001-2006," Med. Res. Rev., 2007, 27(6), pp. 755-796.

Fraley, R., et al., "Entrapment of a bacterial plasmid in phospholipid vesicles: Potential for gene transfer," 1979, Proc. Natl. Acad. Sci. 76, pp. 3348-3352.

Gopal T., "Gene transfer method for transient gene expression, stable transformation, and cotransformation of suspension cell cultures," Mol Cell Biol., May 1985, 5(5), pp. 11880131190.

Graham, F., and van der Eb, A., "A new technique for the assay of infectivity of human adenovirus 5 DNA," Virology, Apr. 1973, vol. 52, Issue 2, pp. 456-457.

Han, G., et al., "Preventative and therapeutic effects of Smad7 on radiation-induced oral mucositis," Nature Medicine, Apr. 2013, vol. 19, No. 4, pp. 421-430.

Harland, R. and Weintraub, H., "Translation of mRNA injected into *Xenopus* oocytes is specifically inhibited by antisense RNA," Sep. 1985, JCB, vol. 101, No. 3, pp. 1094-2099.

Hong, S., et al., "Smad7 binds to the adaptors TAB2 and TAB3 to block recruitment of the kinase TAK1 to the adaptor TRAF2," Nature Immunology, May 2007, vol. 8, No. 5, pp. 504-513.

Imai, E., et al., "Towards gene therapy for renal diseases," Nephrologie, 1998, 19(7), pp. 397-402. Abstract only.

International Search Report and Written Opinion received for PCT/US2011/052499 dated Apr. 9, 2012.

Kaeppler, H., et al., "Silicon carbide fiber-mediated DNA delivery into plant cells," Plan Cell Rep 9, 1990, pp. 415-418.

Kalvala, A., et al., "Enhancement of gene targeting in human cells by intranuclear permeation of the *Saccharomyces cerevisiae* Rad52 protein," Nucl. Acids Res. (2010) 38 (14): e149.

Kato, K., et al., "Direct injection of hepatitis B virus DNA into liver induced hepatitis in adult rats," J Biol Chem, Nov. 1991;266, pp. 22071-22074.

Li, A., et al., "Latent TGFbeta1 overexpression in keratinocytes results in a severe psoriasis-like skin disorder," Apr. 21, 2004, vol. 23, Issue 8, pp. 1770-1781.

Massague, J., et al., "Smad transcription factors," Genes & Dev. 2005. 19: 2783-2810.

Nicolau, C., and Sene, C., "Liposome-mediated DNA transfer in eukaryotic cells: Dependence of the transfer efficiency upon the type of liposomes used and the host cell cycle stage," Biochimica et Biophysica Acta (BBA)—Molecular Cell Research, vol. 721, Issue 2, 11 Oct. 1982, pp. 185-190.

Nicolau, C., et al., "Liposomes as carries for in vivo gene transfer expression," 1987, Meth. Enzymol. 149, pp. 157-176.

Omirulleh, S et al., "Activity of a chimeric promoter with the doubled CaMV 35S enhancer element in protoplast-derived cells and transgenic plants in maize," 1993, Plant Mol Biol 21:415-428.

Potrykus, I., et al., "Molecular and general genetics of a hybrid foreign gene introduced into tobacco by direct gene transfer," Molecular and General Genetics MGG, May 28, 1985, vol. 199, Issue 2, pp. 169-177.

Rippe, R., et al., "DNA-mediated gene transfer into adult rat hepatocytes in primary culture," Mol Cell Biol. Feb. 1990; 10(2): 689013695.

Robbins P., and Ghivizzani S., "Viral vectors for gene therapy," Pharmacol Ther. Oct. 1998;80(1):35-47.

Robbins P., et al., "Viral vectors for gene therapy," Trends Biotechnol. Jan. 1998;16(1):35-40.

Wang, N., et al., "NF-kB," 2008, Anat. Res. vol. 30, No. 2, pp. 141-144. (English Translation Not Available).

Wong, T., et al., "Appearance of B-lactamase activity in animal cells upon liposome-mediated gene transfer," 1980, Gene, 10, pp. 87-94.

Zhang, S., et al., "Smad7 Antagonizes Transforming Growth Factor 3B2 Signaling in the Nucleus by Interfering with Functional Smad-DNA Complex Formation," Mol Cell Biol. Jun. 2007; 27(12): 4488-4499.

Funaki et al., "Ex vivo transfer of Smad7 decreases damage to the corneal endothelium after penetratingkeratoplasty," Japanese Journal of Opthamology, vol. 52, No. 3, Jul. 27, 2008, pp. 204-210.

Han, G et al., "036 Overexpression of Smad7 in Keratinocytes Accelerates Cutaneous Wound Healing," Wound Repair and Regeneration, vol. 12, No. 2, Mar. 2004, pp. A1-A40.

Saika et al., "Transient adenoviral gene transfer of Smad7 prevents formation of ulceration and scarring of the cornea following an alkali exposure in mice," IOVS, May 1, 2005, p. 1165, retrieved from the Internet: URL:http://abstracts,iovs.org/cgi/content/abstract/45/5/1165 retrieved Sep. 25, 2014.

Yamanaka et al., "Gene transfer of Smad7 modulates injury-induced conjunctival wound healing in mice," Molecular vision, Aug. 1, 2006, pp. 841-851.

Extended Search Report for European Application 11827421.6, mailed Dec. 3, 2014.

* cited by examiner

SEQUENCE LISTING

<160> NUMBER OF SEQ ID NOS: 44

<210> SEQ ID NO 1
<211> LENGTH: 23
<212> TYPE: PRT
<213> ORGANISM: Artificial Sequence
<220> FEATURE:
<223> OTHER INFORMATION: Synthetic peptide

<400> SEQUENCE: 1

Gly Ala Leu Phe Leu Gly Trp Leu Gly Ala Ala Gly Ser Thr Met Gly
1               5                   10                  15

Ala Lys Lys Lys Arg Lys Val
            20

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Arg Arg Met Lys Trp Lys Lys
1               5

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide

<400> SEQUENCE: 4

Arg Arg Trp Arg Arg Trp Trp Arg Arg Trp Trp Arg Arg Trp Arg Arg
1               5                   10                  15

<210> SEQ ID NO 5
<211> LENGTH: 18
<212> TYPE: PRT
<213> ORGANISM: Artificial Sequence
<220> FEATURE:
<223> OTHER INFORMATION: Synthetic peptide

<400> SEQUENCE: 5

Arg Gly Gly Arg Leu Ser Tyr Ser Arg Arg Phe Ser Thr Ser Thr
1               5                   10                  15

Gly Arg

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide -continued

```
<400> SEQUENCE: 6

Tyr Gly Arg Lys Lys Arg Arg Gln Arg Arg
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Arg Lys Lys Arg Arg Gln Arg Arg
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Tyr Ala Arg Ala Ala Ala Arg Gln Ala Arg Ala
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Arg Arg Arg Arg Arg Arg Arg Arg
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Lys Lys Lys Lys Lys Lys Lys Lys
1               5

<210> SEQ ID NO 11
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (25)..(25)
<223> OTHER INFORMATION: Xaa can be any naturally occurring amino acid

<400> SEQUENCE: 11

Gly Trp Thr Leu Asn Ser Ala Gly Tyr Leu Leu Gly Lys Ile Asn Leu
1               5                   10                  15

Lys Ala Leu Ala Ala Leu Ala Lys Xaa Ile Leu
            20                  25
```

```
<210> SEQ ID NO 12
<211> LENGTH: 18
<212> TYPE: PRT
<213> ORGANISM: Artificial Sequence
<220> FEATURE:
<223> OTHER INFORMATION: Synthetic peptide

<400> SEQUENCE: 12

Leu Leu Ile Leu Leu Arg Arg Arg Ile Arg Lys Gln Ala Asn Ala His
1               5                   10                  15

Ser Lys

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide

<400> SEQUENCE: 13

Ser Arg Arg His His Cys Arg Ser Lys Ala Lys Arg Ser Arg His His
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Asn Arg Ala Arg Arg Asn Arg Arg Arg Val Arg
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide

<400> SEQUENCE: 15

Arg Gln Leu Arg Ile Ala Gly Arg Arg Leu Arg Gly Arg Ser Arg
1               5                   10                  15

<210> SEQ ID NO 16
<211> LENGTH: 13
<212> TYPE: PRT
<213> ORGANISM: Artificial Sequence
<220> FEATURE:
<223> OTHER INFORMATION: Synthetic peptide

<400> SEQUENCE: 16

Lys Leu Ile Lys Gly Arg Thr Pro Ile Lys Phe Gly Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide

<400> SEQUENCE: 17

Arg Arg Ile Pro Asn Arg Arg Pro Arg Arg
1               5                   10
```

```
<210> SEQ ID NO 18
<211> LENGTH: 18
<212> TYPE: PRT
<213> ORGANISM: Artificial Sequence
<220> FEATURE:
<223> OTHER INFORMATION: Synthetic peptide

<400> SEQUENCE: 18

Lys Leu Ala Leu Lys Leu Ala Leu Lys Ala Leu Lys Ala Ala Leu Lys
1               5                   10                  15

Leu Ala

<210> SEQ ID NO 19
<211> LENGTH: 14
<212> TYPE: PRT
<213> ORGANISM: Artificial Sequence
<220> FEATURE:
<223> OTHER INFORMATION: Synthetic peptide

<400> SEQUENCE: 19

Lys Leu Ala Lys Leu Ala Lys Lys Leu Ala Lys Leu Ala Lys
1               5                   10

<210> SEQ ID NO 20
<211> LENGTH: 27
<212> TYPE: PRT
<213> ORGANISM: Artificial Sequence
<220> FEATURE:
<223> OTHER INFORMATION: Synthetic peptide

<400> SEQUENCE: 20

Gly Ala Leu Phe Leu Gly Phe Leu Gly Ala Ala Gly Ser Thr Asn Gly
1               5                   10                  15

Ala Trp Ser Gln Pro Lys Lys Lys Arg Lys Val
            20                  25

<210> SEQ ID NO 21
<211> LENGTH: 21
<212> TYPE: PRT
<213> ORGANISM: Artificial Sequence
<220> FEATURE:
<223> OTHER INFORMATION: Synthetic peptide

<400> SEQUENCE: 21

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic peptide

<400> SEQUENCE: 22

Leu Lys Lys Leu Leu Lys Lys Leu Leu Lys Lys Leu Leu Lys Lys Leu
1               5                   10                  15

Leu Lys Lys Leu
            20
```

```
<210> SEQ ID NO 23
<211> LENGTH: 34
<212> TYPE: PRT
<213> ORGANISM: Artificial Sequence
<220> FEATURE:
<223> OTHER INFORMATION: Synthetic peptide

<400> SEQUENCE: 23

Gln Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 24
<211> LENGTH: 23
<212> TYPE: PRT
<213> ORGANISM: Artificial Sequence
<220> FEATURE:
<223> OTHER INFORMATION: Synthetic peptide

<400> SEQUENCE: 24

Met Gly Leu Gly Leu His Leu Leu Val Leu Ala Ala Ala Leu Gln Gly
1               5                   10                  15

Ala Lys Ser Lys Arg Lys Val
            20

<210> SEQ ID NO 25
<211> LENGTH: 26
<212> TYPE: PRT
<213> ORGANISM: Artificial Sequence
<220> FEATURE:
<223> OTHER INFORMATION: Synthetic peptide

<400> SEQUENCE: 25

Ala Ala Val Ala Leu Leu Pro Ala Val Leu Leu Ala Leu Leu Ala Pro
1               5                   10                  15

Ala Ala Ala Asn Tyr Lys Lys Pro Lys Leu
            20                  25

<210> SEQ ID NO 26
<211> LENGTH: 28
<212> TYPE: PRT
<213> ORGANISM: Artificial Sequence
<220> FEATURE:
<223> OTHER INFORMATION: Synthetic peptide

<400> SEQUENCE: 26

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 27
<211> LENGTH: 24
<212> TYPE: PRT
<213> ORGANISM: Artificial Sequence
<220> FEATURE:
<223> OTHER INFORMATION: Synthetic peptide
```

```
<400> SEQUENCE: 27

Leu Gly Thr Tyr Thr Gln Asp Phe Asn Lys Phe His Thr Phe Pro Gln
1               5                   10                  15

Thr Ala Ile Gly Val Gly Ala Pro
            20

<210> SEQ ID NO 28
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (24)..(24)
<223> OTHER INFORMATION: Xaa can be any naturally occurring amino acid

<400> SEQUENCE: 28

Asp Pro Lys Gly Asp Pro Lys Gly Val Thr Val Thr Val Thr Val Thr
1               5                   10                  15

Val Thr Gly Lys Gly Asp Pro Xaa Pro Asp
            20                  25

<210> SEQ ID NO 29
<211> LENGTH: 14
<212> TYPE: PRT
<213> ORGANISM: Artificial Sequence
<220> FEATURE:
<223> OTHER INFORMATION: Synthetic peptide

<400> SEQUENCE: 29

Pro Pro Pro Pro Pro Pro Pro Pro Pro Pro Pro Pro Pro Pro
1               5                   10

<210> SEQ ID NO 30
<211> LENGTH: 18
<212> TYPE: PRT
<213> ORGANISM: Artificial Sequence
<220> FEATURE:
<223> OTHER INFORMATION: Synthetic peptide

<400> SEQUENCE: 30

Val Arg Leu Pro Pro Pro Val Arg Leu Pro Pro Pro Val Arg Leu Pro
1               5                   10                  15

Pro Pro

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide

<400> SEQUENCE: 31

Pro Arg Pro Leu Pro Pro Pro Arg Pro Gly
1               5                   10

<210> SEQ ID NO 32
<211> LENGTH: 30
<212> TYPE: PRT
<213> ORGANISM: Artificial Sequence
<220> FEATURE:
<223> OTHER INFORMATION: Synthetic peptide
```

```
<400> SEQUENCE: 32

Ser Val Arg Arg Arg Pro Arg Pro Tyr Leu Pro Arg Pro Arg Pro
1               5                   10                  15

Pro Pro Phe Phe Pro Pro Arg Leu Pro Pro Arg Ile Pro Pro
            20                  25                  30

<210> SEQ ID NO 33
<211> LENGTH: 21
<212> TYPE: PRT
<213> ORGANISM: Artificial Sequence
<220> FEATURE:
<223> OTHER INFORMATION: Synthetic peptide

<400> SEQUENCE: 33

Thr Arg Ser Ser Arg Ala Gly Leu Gln Phe Pro Val Gly Arg Val His
1               5                   10                  15

Arg Leu Leu Arg Lys
            20

<210> SEQ ID NO 34
<211> LENGTH: 23
<212> TYPE: PRT
<213> ORGANISM: Artificial Sequence
<220> FEATURE:
<223> OTHER INFORMATION: Synthetic peptide

<400> SEQUENCE: 34

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 35
<211> LENGTH: 37
<212> TYPE: PRT
<213> ORGANISM: Artificial Sequence
<220> FEATURE:
<223> OTHER INFORMATION: Synthetic peptide

<400> SEQUENCE: 35

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 36
<211> LENGTH: 28
<212> TYPE: PRT
<213> ORGANISM: Artificial Sequence
<220> FEATURE:
<223> OTHER INFORMATION: Synthetic peptide

<400> SEQUENCE: 36

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25
```

```
<210> SEQ ID NO 37
<211> LENGTH: 26
<212> TYPE: PRT
<213> ORGANISM: Artificial Sequence
<220> FEATURE:
<223> OTHER INFORMATION: Synthetic peptide

<400> SEQUENCE: 37

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 38
<211> LENGTH: 14
<212> TYPE: PRT
<213> ORGANISM: Artificial Sequence
<220> FEATURE:
<223> OTHER INFORMATION: Synthetic peptide

<400> SEQUENCE: 38

Ile Asn Leu Lys Ala Leu Ala Ala Leu Ala Lys Lys Ile Leu
1               5                   10

<210> SEQ ID NO 39
<211> LENGTH: 33
<212> TYPE: PRT
<213> ORGANISM: Artificial Sequence
<220> FEATURE:
<223> OTHER INFORMATION: Synthetic peptide

<400> SEQUENCE: 39

Gly Phe Phe Ala Leu Ile Pro Lys Ile Ile Ser Ser Pro Leu Pro Lys
1               5                   10                  15

Thr Leu Leu Ser Ala Val Gly Ser Ala Leu Gly Gly Ser Gly Gly Gln
            20                  25                  30

Glu

<210> SEQ ID NO 40
<211> LENGTH: 15
<212> TYPE: PRT
<213> ORGANISM: Artificial Sequence
<220> FEATURE:
<223> OTHER INFORMATION: Synthetic peptide

<400> SEQUENCE: 40

Leu Ala Lys Trp Ala Leu Lys Gln Gly Phe Ala Lys Leu Lys Ser
1               5                   10                  15

<210> SEQ ID NO 41
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (23)..(23)
<223> OTHER INFORMATION: Xaa can be any naturally occurring amino acid

<400> SEQUENCE: 41

Ser Met Ala Gln Asp Ile Ile Ser Thr Ile Gly Asp Leu Val Lys Trp
1               5                   10                  15

Ile Ile Gln Thr Val Asn Xaa Phe Thr Lys Lys
            20                  25
```

```
<210> SEQ ID NO 42
<211> LENGTH: 41
<212> TYPE: PRT
<213> ORGANISM: Artificial Sequence
<220> FEATURE:
<223> OTHER INFORMATION: Synthetic peptide

<400> SEQUENCE: 42

Leu Leu Gly Asp Phe Phe Arg Lys Ser Lys Glu Lys Ile Gly Lys Glu
1               5                   10                  15

Phe Lys Arg Ile Val Gln Arg Ile Lys Gln Arg Ile Lys Asp Phe Leu
                20                  25                  30

Ala Asn Leu Val Pro Arg Thr Glu Ser
            35                  40

<210> SEQ ID NO 43
<211> LENGTH: 18
<212> TYPE: PRT
<213> ORGANISM: Artificial Sequence
<220> FEATURE:
<223> OTHER INFORMATION: Synthetic peptide

<400> SEQUENCE: 43

Pro Ala Trp Arg Lys Ala Phe Arg Trp Ala Trp Arg Met Leu Lys Lys
1               5                   10                  15

Ala Ala

<210> SEQ ID NO 44
<211> LENGTH: 18
<212> TYPE: PRT
<213> ORGANISM: Artificial Sequence
<220> FEATURE:
<223> OTHER INFORMATION: Synthetic peptide

<400> SEQUENCE: 44

Lys Leu Lys Leu Lys Leu Lys Leu Lys Leu Lys Leu Lys Leu Lys Leu
1               5                   10                  15

Lys Leu
```

THERAPEUTIC APPLICATIONS OF SMAD7

The present application is a national phase application under 35 U.S.C. §371 of International Application No. PCT/US2011/052499, filed Sep. 21, 2011, which claims benefit of priority to U.S. Provisional Application Ser. No. 61/385,445, filed Sep. 22, 2010, the entire contents of which are hereby incorporated by reference.

FEDERALLY FUNDED RESEARCH

This invention was made with government support under grant number GM70966 awarded by the National Institute of Health. The government has certain rights in this invention.

FIELD

The present invention relates general to the fields of oncology and cancer therapies, inflammatory diseases and chronic wound healing. More specifically, the invention relates to methods and compositions for the treatment of inflammatory diseases, chronic wound healing/ulceration, and side effects resulting from chemotherapy and radiation therapy, as well as overexposure to radiation in military/industrial/safety/rescue personnel. In certain embodiments, side effects can include oral mucositis, gut mucositis and bone marrow failure. In particular embodiments, the use of Smad7 (mothers against decapentaplegic-7) protein compositions to prevent or treat the indications described above is provided.

BACKGROUND

Inflammation is a protective attempt by the organism to remove the injurious stimuli and to initiate the healing process. Without inflammation, wounds and infections would never heal. Similarly, progressive destruction of the tissue would compromise the survival of the organism. However, chronic inflammation can also lead to a host of diseases, such as hay fever, atherosclerosis, rheumatoid arthritis, psoriasis and even cancer (e.g., gall bladder carcinoma), and acute inflammation may cause injury through overresponse to an acute stimulus. It is for that reason that inflammation is normally closely regulated by the body.

As indicated above, inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process.

Acute inflammation begins within seconds to minutes following the injury of tissues. The damage may be purely physical, or it may involve the activation of an immune response. Three main processes occur: (a) increased blood flow due to dilation of blood vessels (arterioles) supplying the region; (b) increased permeability of the capillaries, allowing fluid and blood proteins to move into the interstitial spaces; and (c) migration of neutrophils (and perhaps a few macrophages) out of the venules and into interstitial spaces One particular type of inflammatory injury is that stemming from the use of therapeutic agents, many of which are intended to produce inflammation in a diseased tissue or organ, but which unfortunately are rarely able to specifically target those regions. For example, over 80% of oral cancer patients are treated with radiation therapy and at least 75% of these individuals will develop oral mucositis. Oral mucositis also occurs in patients undergoing a hematopoietic stem cell transplant and in other cancer patients requiring radiotherapy and/or chemotherapy, and is often the most severe complication of radiotherapy. Severe oral mucositis is extremely painful and impairs oral intake. Subjects suffering from oral mucositis often require long-term pain medications to alleviate the symptoms of this condition. In addition to inflammation, both chemo- and radiation-induced DNA damage and cell death can bone marrow failure, resulting in death. These are is just two examples, if better regulated, could not only save substantially on healthcare expense, but prevent considerable suffering, loss of patient function, death.

SUMMARY OF THE INVENTION

Thus, in accordance with the present invention, there is provided a method for treating an inflammatory condition and/or tissue damage conditions in a subject comprising providing to the subject a therapeutically effective amount of a Smad7 (mothers against decapentaplegic homolog 7). The Smad7 may be provided as a protein, an expression vector encoding a Smad7 protein, such as a viral or non-viral vector. The composition may comprise a Smad7 protein fused to a protein transduction domain (PTD), and said Smad7 protein fusion may further comprises a regulatory domain that prevents Smad7 function in the absence of an activator, and the method further comprises provision of said activator. The Smad7 may be provided in a formulation on a patch, in a gelatinous composition, in a microsphere, in a microbead or combination thereof. The patch may comprise a biodegradable patch, such as an alginate polymer.

The Smad7 may be provided local to an affected region or systemically. The method may further comprise administering a second mucositis therapy to said subject, such as viscous 2% lidocaine, baking soda solution, saline solution, BAX solution (lidocaine, diphenhyramine, sorbitol and Mylanta), beta carotene, tocopherol, laser irradiation, silver-nitrate, misoprostol, leucovorin, systemic keratinocyte growth factor, pentoxifylline, allopurinol, systemic sucralfate, chlorhexidine gluconate or cryotherapy. The composition may comprise a detectable marker. The inflammatory condition is selected from mucositis, psoriasis, an autoimmune disease, chronic wound, trauma, chemotherapy, radiotherapy or cytokine therapy. The method may further comprise administering said composition to said subject a second time.

In another embodiment, there is provided a method for treating or preventing oral mucositis in a subject undergoing radiation therapy and/or chemotherapy comprising providing to the subject a therapeutically effective amount of a Smad7 (mothers against decapentaplegic homolog 7). The Smad7 may be provided as a protein, an expression vector encoding a Smad7 protein, such as a viral or non-viral vector. The composition may comprise a Smad7 protein fused to a protein transduction domain (PTD), and said Smad7 protein fusion may further comprises a regulatory domain that prevents Smad7 function in the absence of an activator, and the method further comprises provision of said activator. The Smad7 may be provided in a formulation on a patch, in a gelatinous composition, in a microsphere, in a microbead or combination thereof. The patch may comprise a biodegradable patch, such as an alginate polymer.

The Smad7 may be provided local to an affected region or systemically. The method may further comprise administering a second mucositis therapy to said subject, such as viscous 2% lidocaine, baking soda solution, saline solution, BAX solution (lidocaine, diphenhyramine, sorbitol and Mylanta), beta carotene, tocopherol, laser irradiation, silver-nitrate, misoprostol, leucovorin, systemic keratinocyte growth factor, pentoxifylline, allopurinol, systemic sucralfate, chlorhexidine gluconate or cryotherapy. The subject may comprises a subject having a transplant, a subject having cancer or a subject having a condition requiring radiation therapy, such where the subject has cancer and the cancer is selected from the group consisting of oral cancer, colon cancer, breast cancer, head and neck cancer, pancreatic cancer and other cancers treated with upper body radiation or repeated cycles of chemotherapy. The subject may have undergone upper-body radiation. The method may further comprise administering said composition to said subject a second time.

In yet another embodiment, there is provided a kit for treating oral mucositis in a subject comprising (a) a Smad7 agent composition; and (b) a delivery system. The agent may comprises Smad7 protein, optionally fused to a protein transduction domain (PTD), and/or optionally fused to a regulatory domain that prevents Smad7 function in the absence of an activator, and said kit further comprises said activator. The agent may be a Smad7 expression vector, such as a viral or a non-viral expression vector. The delivery system may comprise a gel, salve or patch delivery system. The composition may be lyophilized. The kit may further comprise a pharmaceutically acceptable buffer, solvent or diluent.

Some embodiments concern upregulation of TGF-β and/or NF-κB inhibitory molecules in a subject having or suspected of developing oral mucositis or psoriasis. In certain embodiments, compositions and methods herein concern, induction of Smad7 (mothers against decapentaplegic homolog 7) genes or protein levels or introduction of a Smad7 composition to a subject to treat a subject having a condition disclosed herein. Other embodiments concern over-expression of Smad7 (mothers against decapentaplegic homolog 7) genes and/or induction of Smad7 protein levels in a subject in need of such a treatment. Some embodiments concern using compositions of recombinant forms of Smad7 for expression of Smad7 in a subject.

Other embodiments herein concern treating or preventing oral mucositis in a subject having undergone or that will undergo radiation therapy or chemotherapy. In certain embodiments, these subjects are undergoing treatment for cancer including, but not limited to, oral cancer, head and neck cancer, and other cancers treated with repeated cycles of chemotherapy including, but not limited to, colon cancer, breast cancer, pancreatic cancer, and other cancers.

BRIEF DESCRIPTION OF THE FIGURES

The following drawings form part of the present specification and are included to further demonstrate certain embodiments of the present invention. The embodiments may be better understood by reference to one or more of these drawings in combination with the detailed description of specific embodiments presented herein.

DETAILED DESCRIPTION OF ILLUSTRATIVE EMBODIMENTS

Figure 1:
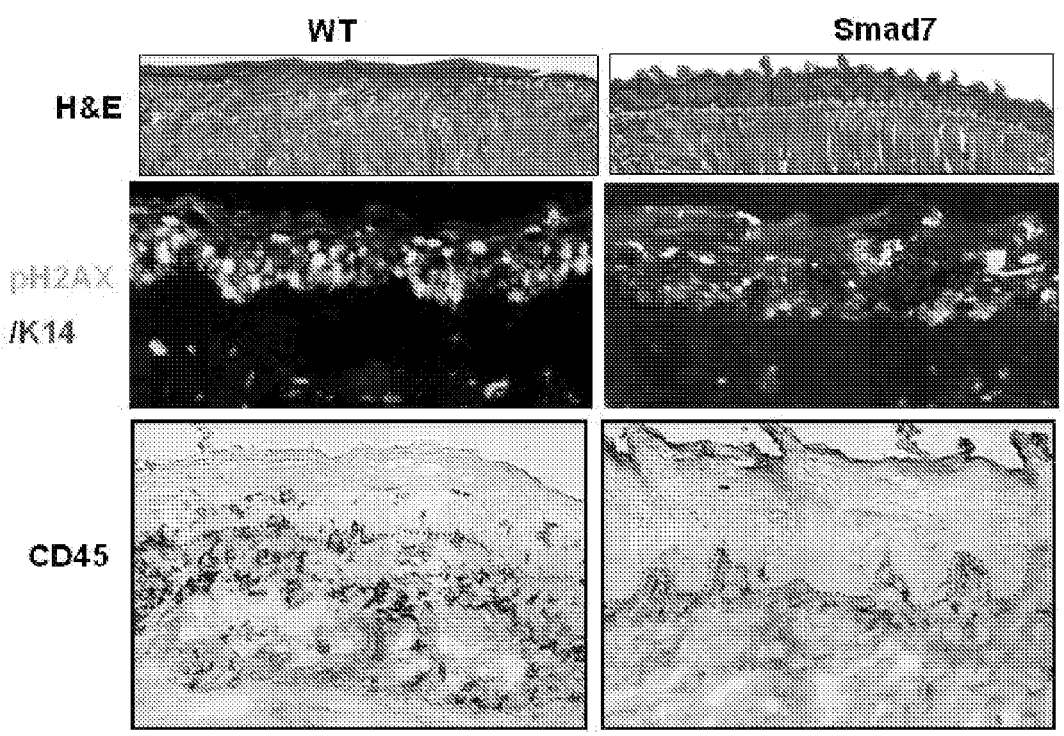
FIG. 1. Resistance to radiation-induced oral mucositis in Smad7 transgenic mice. Dotted lines in H&E highlight the epithelial-stromal boundary. Smad7 mice had an intact oral epithelial layer while wild-type (wt) mice had oral ulcers. pH2AX, a marker for DNA damage (green), was obvious in wt epithelium (K14, red) of oral mucositis, but was significantly reduced in Smad7 transgenic lesion. CD45, stained for total leukocytes (brown), showed severe inflammation in wild-type lesion but a significant reduction in Smad7 transgenic lesion. CD45 immunostaining has non-specific staining in the stratum corneum. For immunostaining, wild-type epithelial images were taken adjacent to the ulcer and Smad7 images were taken from an area with the most leukocytes close to the basement membrane.

As discussed above, over 80% of oral cancer patients are treated with radiation and at least 80% of these individuals develop oral mucositis. In addition, at least 40% and up to 70% of individuals treated with standard chemotherapy regimens or upper-body radiation develop oral mucositis. For example, ~70% colon cancer patients develop severe oral mucositis due to repeated chemotherapy. Hence, a treatment for oral mucositis would be relevant to millions of patients in the United States alone. At present, there remains no truly effective therapy for oral mucositis in cancer patients. Other inflammatory disease states have similar needs for improved therapies.

The Smad7 therapy disclosed below will have a significant therapeutic effect on oral mucositis as well as other chronic, acute or periodic/intermittent inflammatory states. Because this protein has a much stronger effect on inflammation and better promotes wound healing compared to current treatments (e.g. Kepivance®), and because a topical treatment can be user-friendly for example (application of oral solution, gels or patches by patients), these treatments represent a considerable advance. Indeed, since severe oral mucositis patients often require extended hospitalization to manage feeding tubes, dehydration and administering opioids for pain control, the embodiments described herein represent a substantial opportunity to improve the quality of life for patients and significantly reduce the burden of medical cost.

This approach for using Smad7 as a therapeutic agent for oral mucositis is completely unique. In particular, the inventors propose that Smad7 protein can be easily produced recombinantly and used directly or encapsulated into delivery vehicles such as patches, solutions and gels that transduce target cells and exert bioactivities. In addition, this type of Smad7 delivery and thus should show therapeutic efficacies with little side effects. However, viral vector delivery, as well as in vivo induction and activation of Smad7, also are contemplated.

In accordance with various embodiments of the present invention, there may be employed conventional molecular biology, microbiology, and recombinant DNA techniques within the skill of the art. Such techniques are explained fully in the literature. See, e.g., Sambrook et al. (1990).

A. SMAD7 COMPOSITIONS

Mothers against decapentaplegic homolog 7 (Smad7) was previously identified as an antagonist of TGF-β signaling by several mechanisms including: (a) blockade of TGF-β receptor-mediated phosphorylation and nuclear translocation of signaling Smads; (b) increased degradation of TGF-β receptors and signaling Smads through specific ubiquitin-proteasome pathways and (c) inhibition of signaling Smads for their binding to Smad binding elements (SBEs). Smad7 also antagonizes other signaling pathways, like the NF-κB pathway.

Smad7 protein is encoded by the SMAD7 gene (SEQ ID NOS: 1 and 2). Like many other TGF-β family members, Smad7 is involved in cell signalling. It is a TGF-β type 1 receptor antagonist. It blocks TGF-β1 and activin associating with the receptor, blocking access to Smad2. It is an inhibitory Smad (1-SMAD) and is enhanced by SMURF2. Smad7 also enhances muscle differentiation.

In one embodiment, the present invention relates to Smad7 protein compositions. In addition to the entire Smad7 molecule, the present invention also relates to fragments of the polypeptide that retain the anti-inflammatory activity. Fragments may be generated by genetic engineering of translation stop sites within the coding region (discussed below). Alternatively, treatment of the Smad7 molecule with proteolytic enzymes, known as proteases, can produces a variety of N-terminal, C-terminal and internal fragments. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

Variants of Smad7 are also contemplated—these can be substitutional, insertional or deletion variants. Deletion variants lack one or more residues of the native protein which are not essential for activity, including the truncation mutants described above. Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, each amino acid can be changed or substituted with a different amino acid. In making substitutional variants, the hydropathic index, hydrophilicity, charge and size are normally considered.

A specialized kind of variant is the fusion protein. This molecule generally has all or a substantial portion of the native molecule, linked at the N- or C-terminus, to all or a portion of a second polypeptide. For example, fusions may employ leader sequences from other species to permit the recombinant expression of a protein in a heterologous host. Another useful fusion includes the addition of a functionally active domain, such as an antibody epitope, to facilitate purification of the fusion protein. Another type of fusion includes attaching a domain that can act as the target for an activating or inactivating ligand, thereby permitting control of the fusion protein's function once delivered to a subject. Such domains include, for example, steroid ligand binding (e.g., ER, PR, GR), which can be activated by small molecules, e.g., 4-hydroxyl tomaxifen or RU486 that are either uniquely able to activate those steroid ligand binding domains and/or do not exist in nature and will therefore enable full control of the Smad7 function by the presence of these small molecules.

Another specific form of a fusion protein finding particular utility in the present invention is a fusion including a protein transduction domain (PTD), also called a cell delivery domain or cell transduction domain. Such domains have been described in the art and are generally characterized as short amphipathic or cationic peptides and peptide derivatives, often containing multiple lysine and arginine resides (Fischer, 2007). Perhaps the best known PTD is the TAT protein from HIV, as well HSV VP16. Other examples are shown in Table 1, below.

TABLE 1

| PROTEIN TRANSDUCTION DOMAINS | |
| --- | --- |
| GALFLGWLGAAGSTMGAKKKRKV | 1 |
| RQIKIWFQNRRMKWKK | 2 |
| RRMKWKK | 3 |
| RRWRRWWRRWWRRWRR | 4 |
| RGGRLSYSRRRFSTSTGR | 5 |
| YGRKKRRQRRR | 6 |
| RKKRRQRRR | 7 |
| YARAAARQARA | 8 |

TABLE 1-continued

PROTEIN TRANSDUCTION DOMAINS

| Sequence | SEQ ID NO: |
|---|---|
| RRRRRRRR | 9 |
| KKKKKKKK | 10 |
| GWTLNSAGYLLGKINLKALAALAKKIL | 11 |
| LLILLRRRIRKQANAHSK | 12 |
| SRRHHCRSKAKRSRHH | 13 |
| NRARRNRRRVR | 14 |
| RQLRIAGRRLRGRSR | 15 |
| KLIKGRTPIKFGK | 16 |
| RRIPNRRPRR | 17 |
| KLALKLALKALKAALKLA | 18 |
| KLAKLAKKLAKLAK | 19 |
| GALFLGFLGAAGSTNGAWSQPKKKRKV | 20 |
| KETWWETWWTEWSQPKKKRKV | 21 |
| LKKLLKKLLKKLLKKLLKKL | 22 |
| QAATATRGRSAASRPTERPRAPARSASRPRRPVE | 23 |
| MGLGLHLLVLAAALQGAKSKRKV | 24 |
| AAVALLPAVLLALLAPAAANYKKPKL | 25 |
| MANLGYWLLALFVTMWTDVGLCKKRPKP | 26 |
| LGTYTQDFNKFHTFPQTAIGVGAP | 27 |
| DPKGDPKGVTVTVTVTGKGDPXPD | 28 |
| PPPPPPPPPPPPPP | 29 |
| VRLPPPVRLPPPVRLPPP | 30 |
| PRPLPPPRPG | 31 |
| SVRRRPRPPYLPRPRPPPFFPPRLPPRIPP | 32 |
| TRSSRAGLQFPVGRVHRLLRK | 33 |
| GIGKFLHSAKKFGKAFVGEIMNS | 34 |
| KWKLFKKIEKVGQNIRDGIIKAGPAVAVVGQATQIAK | 35 |
| ALWMTLLKKVLKAAAKAALNAVLVGANA | 36 |
| GIGAVLKVLTTGLPALISWIKRKRQQ | 37 |
| INLKALAALAKKIL | 38 |
| GFFALIPKIISSPLPKTLLSAVGSALGGSGGQE | 39 |
| LAKWALKQGFAKLKS | 40 |
| SMAQDIISTIGDLVKWIIQTVNXFTKK | 41 |
| LLGDFFRKSKEKIGKEFKRIVQRIKQRIKDFLANLVPRTES | 42 |
| PAWRKAFRWAWRMLKKAA | 43 |
| KLKLKLKLKLKLKLKL | 44 |

B. NUCLEIC ACIDS, VECTORS AND RECOMBINANT EXPRESSION

The present invention also provides, in another embodiment, genes encoding Smad7. In addition to the identified SMAD7 gene, it should be clear that the present invention is not limited to the specific nucleic acids disclosed herein. As discussed below, a "Smad7 gene" may contain a variety of different bases and yet still produce a corresponding polypeptide that is functionally indistinguishable from, and in some cases structurally identical to, the human gene disclosed herein.

1. Nucleic Acids Encoding Smad7

Nucleic acids according to the present invention may represent an entire Smad7 gene, a domain of Smad7 that expresses a tumor suppressing function, or any other fragment of the Smad7 sequences set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "minigenes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

As used in this application, the term "a nucleic acid encoding a Smad7" refers to a nucleic acid molecule that has been isolated free of total cellular nucleic acid. The term "functionally equivalent codon" is used herein to refer to codons that encode the same amino acid, such as the six codons for arginine or serine, and also refers to codons that encode biologically equivalent amino acids, as discussed in the following pages.

Allowing for the degeneracy of the genetic code, sequences that have at least about 50%, usually at least about 60%, more usually about 70%, most usually about 80%, preferably at least about 90% and most preferably about 95% of nucleotides that are identical to the Smad7 sequences. Sequences that are essentially the same as Smad 7 also may be functionally defined as sequences that are capable of hybridizing to a nucleic acid segment containing the complement of Smad7 under standard conditions.

The DNA segments of the present invention include those encoding biologically functional equivalent Smad7 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

2. Vectors for Cloning, Gene Transfer and Expression

Within certain embodiments, expression vectors are employed to express the Smad7 polypeptide product, which can then be purified for various uses. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al. (1989) and Ausubel et al. (1994), both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism, including promoters and enhancers. In addition to control sequences that govern transcription and translation, vectors and expression vectors may contain nucleic acid sequences that serve other functions, such as transcription termination signals and poly-adenylation sites.

The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, lentiviruses, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670, 488). The various viral vectors present specific advantages and disadvantages, depending on the particular gene-therapeutic application.

Suitable non-viral methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464, 765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

5. Expression Systems

Numerous expression systems exist that comprise at least a part or all of the compositions discussed above. Prokaryote-and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented.

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. INFLAMMATORY DISEASE STATES

1. Chronic Wounds

A chronic wound is a wound that does not heal in an orderly set of stages and in a predictable amount of time the way most wounds do; wounds that do not heal within three months are often considered chronic. Chronic wounds seem to be detained in one or more of the phases of wound healing. For example, chronic wounds often remain in the inflammatory stage for too long. In acute wounds, there is a precise balance between production and degradation of molecules such as collagen; in chronic wounds this balance is lost and degradation plays too large a role.

Chronic wounds may never heal or may take years to do so. These wounds cause patients severe emotional and physical stress as well as creating a significant financial burden on patients and the whole healthcare system. Acute and chronic wounds are at opposite ends of a spectrum of wound healing types that progress toward being healed at different rates. The vast majority of chronic wounds can be classified into three categories: venous ulcers, diabetic, and pressure ulcers. A small number of wounds that do not fall into these categories may be due to causes such as radiation poisoning or ischemia.

Venous and Arterial Ulcers.

Venous ulcers, which usually occur in the legs, account for about 70% to 90% of chronic wounds and mostly affect the elderly. They are thought to be due to venous hypertension caused by improper function of valves that exist in the veins to prevent blood from flowing backward. Ischemia results from the dysfunction and, combined with reperfusion injury, causes the tissue damage that leads to the wounds.

Diabetic Ulcers.

Another major cause of chronic wounds, diabetes, is increasing in prevalence. Diabetics have a 15% higher risk for amputation than the general population due to chronic ulcers. Diabetes causes neuropathy, which inhibits nociception and the perception of pain. Thus patients may not initially notice small wounds to legs and feet, and may therefore fail to prevent infection or repeated injury. Further, diabetes causes immune compromise and damage to small blood vessels, preventing adequate oxygenation of tissue, which can cause chronic wounds. Pressure also plays a role in the formation of diabetic ulcers.

Pressure Ulcers.

Another leading type of chronic wounds is pressure ulcers, which usually occur in people with conditions such as paralysis that inhibit movement of body parts that are commonly subjected to pressure such as the heels, shoulder blades, and sacrum. Pressure ulcers are caused by ischemia that occurs when pressure on the tissue is greater than the pressure in capillaries, and thus restricts blood flow into the area. Muscle tissue, which needs more oxygen and nutrients than skin does, shows the worst effects from prolonged pressure. As in other chronic ulcers, reperfusion injury damages tissue.

Chronic wounds may affect only the epidermis and dermis, or they may affect tissues all the way to the fascia. They may be formed originally by the same things that cause acute ones, such as surgery or accidental trauma, or they may form as the result of systemic infection, vascular, immune, or nerve insufficiency, or comorbidities such as neoplasias or metabolic disorders. The reason a wound becomes chronic is that the body's ability to deal with the damage is overwhelmed by factors such as repeated trauma, continued pressure, ischemia, or illness.

Though much progress has been accomplished in the study of chronic wounds lately, advances in the study of their healing have lagged behind expectations. This is partly because animal studies are difficult because animals do not get chronic wounds, since they usually have loose skin that quickly contracts, and they normally do not get old enough or have contributing diseases such as neuropathy or chronic debilitating illnesses. Nonetheless, current researchers now understand some of the major factors that lead to chronic wounds, among which are ischemia, reperfusion injury, and bacterial colonization.

Ischemia.

Ischemia is an important factor in the formation and persistence of wounds, especially when it occurs repetitively (as it usually does) or when combined with a patient's old age. Ischemia causes tissue to become inflamed and cells to release factors that attract neutrophils such as interleukins, chemokines, leukotrienes, and complement factors.

While they fight pathogens, neutrophils also release inflammatory cytokines and enzymes that damage cells. One of their important jobs is to produce Reactive Oxygen Species (ROS) to kill bacteria, for which they use an enzyme called myeloperoxidase. The enzymes and ROS produced by neutrophils and other leukocytes damage cells and prevent cell proliferation and wound closure by damaging DNA, lipids, proteins, the ECM, and cytokines that speed healing. Neutrophils remain in chronic wounds for longer than they do in acute wounds, and contribute to the fact that chronic wounds have higher levels of inflammatory cytokines and ROS. Since wound fluid from chronic wounds has an excess of proteases and ROS, the fluid itself can inhibit healing by inhibiting cell growth and breaking down growth factors and proteins in the ECM.

Bacterial Colonization.

Since more oxygen in the wound environment allows white blood cells to produce ROS to kill bacteria, patients with inadequate tissue oxygenation, for example those who suffered hypothermia during surgery, are at higher risk for infection. The host's immune response to the presence of bacteria prolongs inflammation, delays healing, and damages tissue. Infection can lead not only to chronic wounds but also to gangrene, loss of the infected limb, and death of the patient.

Like ischemia, bacterial colonization and infection damage tissue by causing a greater number of neutrophils to enter the wound site. In patients with chronic wounds, bacteria with resistances to antibiotics may have time to develop. In addition, patients that carry drug resistant bacterial strains such as methicillin-resistant *Staphylococcus aureus* (MRSA) have more chronic wounds.

Growth Factors and Proteolytic Enzymes.

Chronic wounds also differ in makeup from acute wounds in that their levels of proteolytic enzymes such as elastase, and matrix metalloproteinases (MMPs) are higher, while their concentrations of growth factors such as Platelet-derived growth factor and Keratinocyte Growth Factor are lower.

Since growth factors (GFs) are imperative in timely wound healing, inadequate GF levels may be an important factor in chronic wound formation. In chronic wounds, the formation and release of growth factors may be prevented, the factors may be sequestered and unable to perform their metabolic roles, or degraded in excess by cellular or bacterial proteases.

Chronic wounds such as diabetic and venous ulcers are also caused by a failure of fibroblasts to produce adequate ECM proteins and by keratinocytes to epithelialize the wound. Fibroblast gene expression is different in chronic wounds than in acute wounds.

Though all wounds require a certain level of elastase and proteases for proper healing, too high a concentration is damaging. Leukocytes in the wound area release elastase, which increases inflammation, destroys tissue, proteoglycans, and collagen, and damages growth factors, fibronectin, and factors that inhibit proteases. The activity of elastase is increased by human serum albumin, which is the most abundant protein found in chronic wounds. However, chronic wounds with inadequate albumin are especially unlikely to heal, so regulating the wound's levels of that protein may in the future prove helpful in healing chronic wounds.

Excess matrix metalloproteinases, which are released by leukocytes, may also cause wounds to become chronic. MMPs break down ECM molecules, growth factors, and protease inhibitors, and thus increase degradation while reducing construction, throwing the delicate compromise between production and degradation out of balance.

2. Acute Wounds/Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present invention provides to treatment of trauma, including both pre-treatment (in the case of a medical procedure) and treatment after trauma injury as occurred.

Surgery.

Surgery uses operative manual and instrumental techniques on a patient to investigate and/or treat a pathological condition such as disease or injury, to help improve bodily function or appearance, or sometimes for some other reason. The present invention can address trauma resulting from surgeries, as defined further below.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. All forms of surgery are considered invasive procedures; so-called noninvasive surgery usually refers to an excision that does not penetrate the structure being addressed (e.g., laser ablation of the cornea) or to a radiosurgical procedure (e.g., irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classed by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty. By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

3. Autoimmune/Inflammatory Disease

The present invention contemplates the treatment of a variety of autoimmune and/or inflammatory disease states such as spondyloarthropathy, ankylosing spondylitis, psoriatic arthritis, reactive arthritis, enteropathic arthritis, ulcerative colitis, Crohn's disease, irritable bowel disease, inflammatory bowel disease, rheumatoid arthritis, juvenile rheumatoid arthritis, familial Mediterranean fever, amyotrophic lateral sclerosis, Sjogren's syndrome, early arthritis, viral arthritis, multiple sclerosis, or psoriasis. The diagnosis and treatment of these diseases are well documented in the literature.

4. Chemotherapy, Radiotherapy and Cytokine Therapy Toxicity

Various forms of cancer therapy, including chemotherapy, radiation, and cytokines, are associated with toxicity, sometimes severe, in the cancer patient. To the extent that the toxicity is caused at least in part by the extracellular actions of histones, the present invention seeks to reduce this toxicity using the pharmaceutical compositions of the present invention, thereby reducing or alleviating discomfort on the part of the patient, as well as permitting higher doses of the therapy.

Oral cancer, the $6^{th}$ most common cancer worldwide, is a subtype of head and neck cancer, is any cancerous tissue growth located in the oral cavity. It may arise as a primary lesion originating in any of the oral tissues, by metastasis from a distant site of origin, or by extension from a neighboring anatomic structure, such as the nasal cavity or the oral cancers may originate in any of the tissues of the mouth, and may be of varied histologic types: teratoma, adenocarcinoma derived from a major or minor salivary gland, lymphoma from tonsillar or other lymphoid tissue, or melanoma from the pigment-producing cells of the oral mucosa. There are several types of oral cancers, but around 90% are squamous cell carcinomas, originating in the tissues that line the mouth and lips. Oral or mouth cancer most commonly involves the tongue. It may also occur on the floor of the mouth, cheek lining, gingiva (gums), lips, or palate (roof of the mouth). Most oral cancers look very similar under the microscope and are called squamous cell carcinoma. These are malignant and tend to spread rapidly.

Over 80% of oral cancer patients are treated with radiation therapy and at least 75% of these individuals will develop oral mucositis. Oral mucositis is a chronic oral ulceration. This disease frequently occurs in radiation-treated patients of all cancer types, patients radiation-treated for organ transplants (to eliminate rejection of the transplants), and patients undergoing routine chemotherapy. Severe oral mucositis is extremely painful and impairs food/liquid intake, hence is often the most severe complication of cancer therapy. Oral mucositis is a major factor in determining the maximum dose possible of radiation and chemotherapy to the head and neck region; it can significantly complicate cancer treatment, extend hospitalization, decrease quality of life and increase costs. Currently, there is no established therapy to effectively treat severe oral mucositis. To date, Kepivance®, a recombinant protein of human keratinocyte growth factor (KGF), is the only FDA approved drug through i.v. injections for severe oral mucositis in bone-marrow transplant patients, and its use in cancer patients remains to be determined. Hence, this drug is available for only 4% of the at-risk population. It also suffers from the need for medical service providers due to the i.v. route. Other potential therapies include topical rinses, such as viscous 2% lidocaine rinses, or baking soda and saline solutions, or a cocktail solution, for instance BAX (lidocaine, diphenhyramine, sorbitol and Mylanta). Other investigative or mucoprotective adjuvant therapies include but are not limited to, beta carotene, tocopherol, laser irradiation, prophylactic brushing the oral mucosa with silver-nitrate, misoprostol, leucovorin, systemic KGF, pentoxifylline, allopurinol mouthwash, systemic sucralfate, chlorhexidine gluconate, and cryotherapy.

Chemotherapy and radiation induced gut mucositis is an inflammatory condition that arises as a result of the acute death of rapidly dividing intestinal epithelial cells. Most chemotherapeutic drugs used for treatment of solid tumors, alone, in a combination of drugs, or with radiation, will result in the death of a large number of intestinal epithelial cells. The clinical manifestations of the ensuing mucositis include digestive symptoms such as nausea and vomiting, serious diarrhea, acute weight loss and wasting. This is fast becoming one of the limiting factors for administering chemotherapy for many cancer patients. The ability of Tat-Smad7 to protect intestinal epithelial cells from either chemotherapeutic agents, radiation, or a combinations of those, will significantly decrease the undesirable side effects of cancer therapies, and enable more aggressive ways to treat the disease with existing tools.

Bone marrow failure syndromes are a set of conditions that develop when the hematopoietic stem cell compartment is compromised and fails to give rise to normal cell types. Bone marrow failure occurs as a result of inherited genetic abnormalities, exposure to a noxious substance, such as toxins, chemicals or viruses. Although the nature and identity of environmental factors that can lead to the development of acquired bone marrow failure is still not completely understood, a few factors have been linked to the development of acquired bone marrow failure among military personnel including exposure to mustard gas, ionizing radiation, and infectious agents such as visceral leishmaniasis or African trypanosomiasis. The best approach for management of bone marrow failure syndromes is still the transplantation of HSCs, unless a sufficient number of the remaining resident BM HSCs can be spared from these stresses and encouraged to repopulate the hematopoietic compartment. The modulation of Smad 7, as described here, should enable for the deliberate protection of the remaining resident HSCs in patients that exhibit clinical signs consistent with bone marrow failure.

5. Combination Anti-Inflammatory Therapies

It is common in many fields of medicine to treat a disease with multiple therapeutic modalities, often called "combination therapies." Inflammatory disease are no exception. To treat inflammatory disorders using the methods and compositions of the present invention, one would generally contact a target cell, organ or subject with a Smad7 protein, expression construct or activator and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the Smad7 agent and the other includes the other agent.

Alternatively, the Smad7 agent may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the Smad7 agent or the other therapy will be desired. Various combinations may be employed, where the Smad7 agent is "A," and the other therapy is "B," as exemplified below:

| | | | | | |
|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are contemplated. Other agents suitable for use in a combined therapy against an inflammatory disorder include steroids, glucocorticoids, non-steriodal anti-inflammatory drugs (NSAIDS; including COX-1 and COX-2 inhibitors), aspirin, ibuprofen, and naproxen. Analgesics are commonly associated with anti-inflammatory drugs but which have no anti-inflammatory effects. An example is paracetamol, called acetaminophen in the U.S. and sold under the brand name of Tylenol. As opposed to NSAIDS, which reduce pain and inflammation by inhibiting COX enzymes, paracetamol has recently been shown to block the reuptake of endocannabinoids, which only reduces pain, likely explaining why it has minimal effect on inflammation. A particular agent for combination use is an anti-TGF-β antibody.

The skilled artisan is directed to "Remington's Pharmaceutical Sciences" 15th Edition, chapter 33, in particular pages 624-652, 1990. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating inflammation.

6. Combinations with Cancer Therapy

As discussed above, the invention has particular relevance to the treatment of DNA damage and/or inflammation resulting from certain anti-cancer therapies. Thus, in particular, the invention may be applied as a combination to with cancer therapies. While cancer therapies address the cancer, they unfortunately cause serious side effects. As such, the Smad7 agents of the present invention can be used advantageously in combination with such cancer therapies. This process may involve contacting the cells, organ or patient with the agents/therapies at the same time, including by contacting the cells, organ or patient with a single composition or pharmacological formulation that includes both agents, or with two distinct compositions or formulations at the same time, wherein one composition includes the Smad7 agent and the other includes the other agent. Alternatively, analogous to the chart set forth above, the compositions can be delivered at different times, including repeated doses of one or both agents.

Agents or factors suitable for use in a combined therapy include any chemical compound or treatment method that induces DNA damage when applied to a cell. Such agents and factors include radiation and waves that induce DNA damage such as, irradiation, microwaves, electronic emissions, and the like. A variety of chemical compounds, also described as "chemotherapeutic" or "genotoxic agents," are intended to be of use in the combined treatment methods disclosed herein. In treating cancer according to the invention, one would contact the tumor cells with an agent in addition to the expression construct. This may be achieved by irradiating the localized tumor site; alternatively, the tumor cells may be contacted with the agent by administering to the subject a therapeutically effective amount of a pharmaceutical composition.

Various classes of chemotherapeutic agents are comtemplated for use with in combination with peptides of the present invention. For example, selective estrogen receptor antagonists ("SERMs"), such as Tamoxifen, 4-hydroxy Tamoxifen (Afimoxfene), Falsodex, Raloxifene, Bazedoxifene, Clomifene, Femarelle, Lasofoxifene, Ormeloxifene, and Toremifene.

Chemotherapeutic agents contemplated to be of use, include, e.g., camptothecin, actinomycin-D, mitomycin C. The invention also encompasses the use of a combination of one or more DNA damaging agents, whether radiation-based or actual compounds, such as the use of X-rays with cisplatin or the use of cisplatin with etoposide. The agent may be prepared and used as a combined therapeutic composition, or kit, by combining it with a MUC1 peptide, as described above.

Heat shock protein 90 is a regulatory protein found in many eukaryotic cells. HSP90 inhibitors have been shown to be useful in the treatment of cancer. Such inhibitors include Geldanamycin, 17-(Allylamino)-17-demethoxygeldanamycin, PU-H71 and Rifabutin.

Agents that directly cross-link DNA or form adducts are also envisaged. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for doxorubicin, to 35-50 mg/m$^2$ for etoposide intravenously or double the intravenous dose orally. Microtubule inhibitors, such as taxanes, also are contemplated. These molecules are diterpenes produced by the plants of the genus *Taxus*, and include paclitaxel and docetaxel.

Epidermal growth factor receptor inhibitors, such as Iressa, mTOR, the mammalian target of rapamycin, also known as FK506-binding protein 12-rapamycin associated protein 1 (FRAP1) is a serine/threonine protein kinase that regulates cell growth, cell proliferation, cell motility, cell survival, protein synthesis, and transcription. Rapamycin and analogs thereof ("rapalogs") are therefore contemplated for use in combination cancer therapy in accordance with the present invention.

Another possible combination therapy with the peptides claimed herein is TNF-α (tumor necrosis factor-alpha), a cytokine involved in systemic inflammation and a member of a group of cytokines that stimulate the acute phase reaction. The primary role of TNF is in the regulation of immune cells. TNF is also able to induce apoptotic cell death, to induce inflammation, and to inhibit tumorigenesis and viral replication.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, x-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In addition to combining Smad7 therapies with chemo- and radiotherapies, it also is contemplated that combination with immunotherapy, hormone therapy, toxin therapy and surgery. In particular, one may employ targeted therapies such as Avastin, Erbitux, Gleevec, Herceptin and Rituxan.

In other embodiments, to assess the roles and mechanisms of Smad7 within the context of oral mucositis, "gene-switch" transgenic mouse models were developed to allow control of the level and duration of Smad7 transgene expression specifically in oral epithelia. In accordance with these embodiments, these models may be used to test other genes or downstream molecules for their effects on oral epithelia and oral mucosa. Thus, these models can be used for, but are not limited to, further analysis of oral wound healing biology and testing therapeutic approaches to oral wound healing. Molecular Smad7 targets identified in these studies can provide additional therapeutic targets for subjects suffering from oral mucositis. Models and resources developed herein can provide unique tools for analytical studies to identify biomarkers and therapeutic targets related to Smad7 overexpression and control, for example, downstream molecules turned on or bound by Smad7 can be identified as additional therapeutic targets for example, to treat oral mucositis, psoriasis and other conditions aggravated by TGF-β activities and NFκB activities.

D. FORMULATIONS AND ROUTES OF DELIVERY

Where clinical applications are contemplated, it will be necessary to prepare pharmaceutical compositions—proteins, expression vectors, virus stocks, proteins and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The formulations are easily administered in a variety of dosage forms. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

In accordance with these embodiments, oral delivery materials can also include creams, salves, ointments, patches, liposomes, nanoparticles, microparticles, timed-release formulations and other materials known in the art for delivery to the oral cavity and/or to the skin of a subject for treatment and/or prevention of a condition disclosed herein. Certain embodiments concern using a biodegradable oral patch delivery system or gelatinous material. These compositions can be a liquid formulation or a pharmaceutically acceptable delivery system treated with a formulation of these compositions, and may also include activator/inducers.

In certain embodiments, a patch contemplated herein may be a slowly dissolving or a time-released patch. In accordance with these embodiments, a slowly dissolving patch can be an alginate patch. In certain examples, a patch may contain a detectible indicator dye or agent such as a fluorescent agent. In other embodiments, a tag (e.g. detectible tag such as a biotin or fluorescently tagged agent) can be associated with a treatment molecule in order to detect the molecule after delivery to the subject. In certain embodiments, one or more oral delivery patches or other treatment contemplated herein may be administered to a subject 3 times daily, 2 times daily, once a day, every other day, weekly, and the like, depending on need of the subject assessed by a health professional. Patches contemplated herein may be oral-biodegradable patches or patches for exterior use that may or may not degrade. Patches contemplated herein may be 1 mm, 2 mm, 3 mm, 4 mm to 5 mm in size or more depending on need. In addition, skin patches are contemplated herein for use in a subject suffering from psoriasis. In treating psoriasis and chronic wounds, Smad7 can be delivered topically using vehicles such as glycerol, carboxymethycellulose. It can also use transdermal system (e.g., commercially available from 3M) for delivery. Subcutaneous injection into the lesion (in normal saline or PBS) can also be used It is contemplated that any molecular biology, cellular biology or biochemical technique known in the art may be used to generate and/or test treatments contemplated herein. In addition, protein chemistry techniques are contemplated to assess utility of treatments in model systems developed herein (e.g. mouse model system).

E. KITS

In certain embodiments, a kit contemplated herein may include compositions discussed above for treating a subject having a condition contemplated herein, such as oral mucositis or psoriasis. The kits can include one or more containers containing the therapeutic compositions. Any of the kits will generally include at least one vial, test tube, flask, bottle, syringe or other container, into which compositions may be preferably and/or suitably aliquoted. Kits herein may also include a kit for assessing biological targets that contribute to a condition contemplated herein.

F. EXAMPLES

The following examples are included to illustrate various embodiments. It should be appreciated by those of skill in the art that the techniques disclosed in the examples that follow represent techniques discovered to function well in the practice of the claimed methods, compositions and apparatus. However, those of skill in the art should, in light of the present disclosure, appreciate that many changes may be made in the specific embodiments which are disclosed and still obtain a like or similar result without departing from the spirit and scope of the invention.

Smad7 transgenic mice have been described with multiple functions of Smad7. This mouse model is crucial for understanding that Smad7 has a potent effect in oral mucositis. Smad7 promotes healing of oral wounds. Based on these findings, if Smad7 can provide protection from oral mucositis can be assessed. Smad7 transgenic mice and their littermates were exposed to radiation. In non-transgenic littermates, all died of oral mucositis in 10 days due to loss of oral intake-associated dehydration and starvation. In contrast, none of the Smad7 transgenic mice formed oral mucositis (FIG. 1). Based on this data, local pharmacologic delivery of Smad7 can be used to treat oral mucositis. In other embodiments, a Smad7 expression plasmid with either replication-free viral vector or non-viral vector, can be used to treat oral mucositis.

Figure 2:
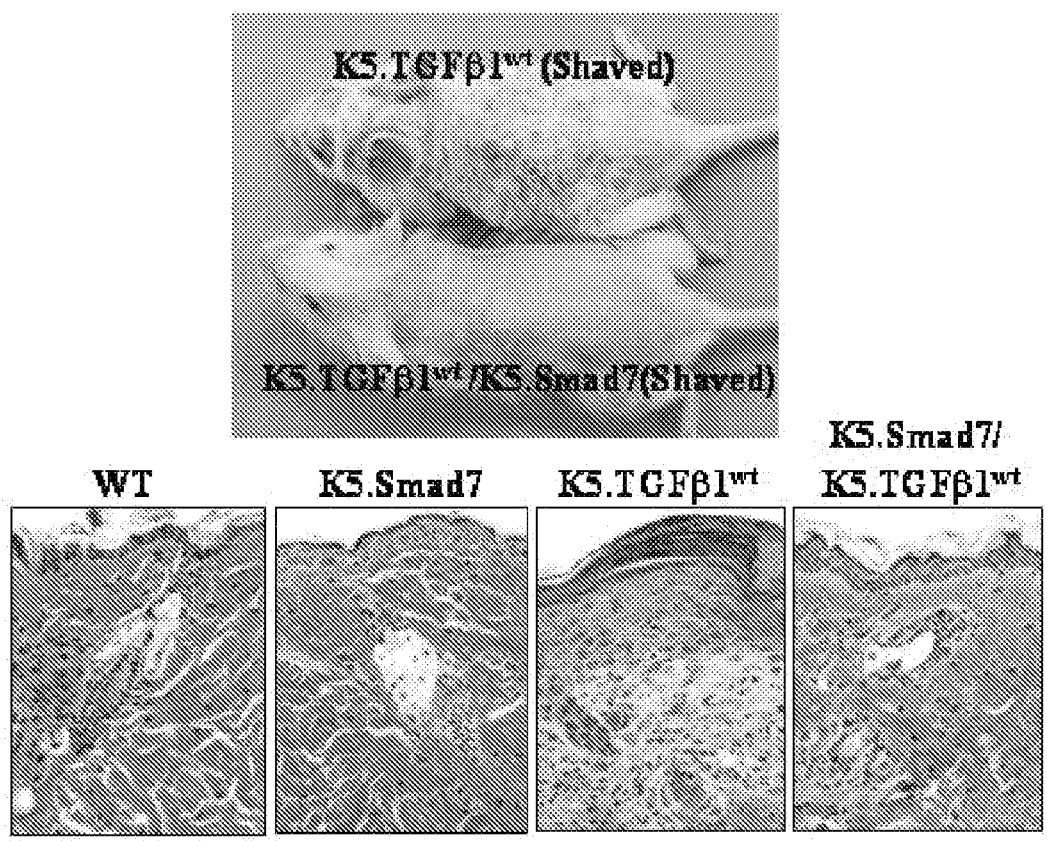
FIG. 2. Smad7 transgene expression reversed psoriasis of K5.TGFβ1$^{wt}$ mice. Upper panel: gross appearance of a 3 month-old K5.TGFβ1$^{wt}$/K5.Smad7 mouse (smooth skin) and its K5.TGFβ1$^{wt}$ littermate (inflamed skin, eyes and ears). Lower panel: while K5.TGFβ1$^{wt}$ skin exhibited epidermal hyperplasia and skin inflammation, K5.Smad7 skin and K5.Smad7/TGFβ1$^{wt}$ skin are similar to normal wild-type (WT) skin.

Preliminary data show that Smad7 promotes healing mainly through promoting epithelial cell migration into the wounds and protecting cells against DNA damage (FIG. 1), the latter is tumor suppressive. Smad7 has been shown to inhibit cancer metastasis and unpublished data show Smad7 overexpression in mice does not increase susceptibility to cancer. Given that unresolved inflammation is one of the major causes of failed healing in oral mucositis, the strong effect of Smad7 can significantly promote healing of oral mucositis. In one exemplary example, transgenic mice were generated with severe skin psoriasis, and these mice die within 6 months due to severe itch-associated wasting syndrome. When these psoriasis mice were bred with Smad7 transgenic mice (the same showing resistance to radiation-induced oral mucositis in FIG. 1), skin inflammation was absent and the mice lived a normal lifespan (FIG. 2). Interestingly, in both cases (FIGS. 1-2), Smad7 transgene expression level is only 2-fold of endogenous Smad7, suggesting that a low dose of Smad7 is sufficient for therapeutic effect. Smad7 oral patch/gel can be administered by patients with minimal systemic effects.

Figure 3:
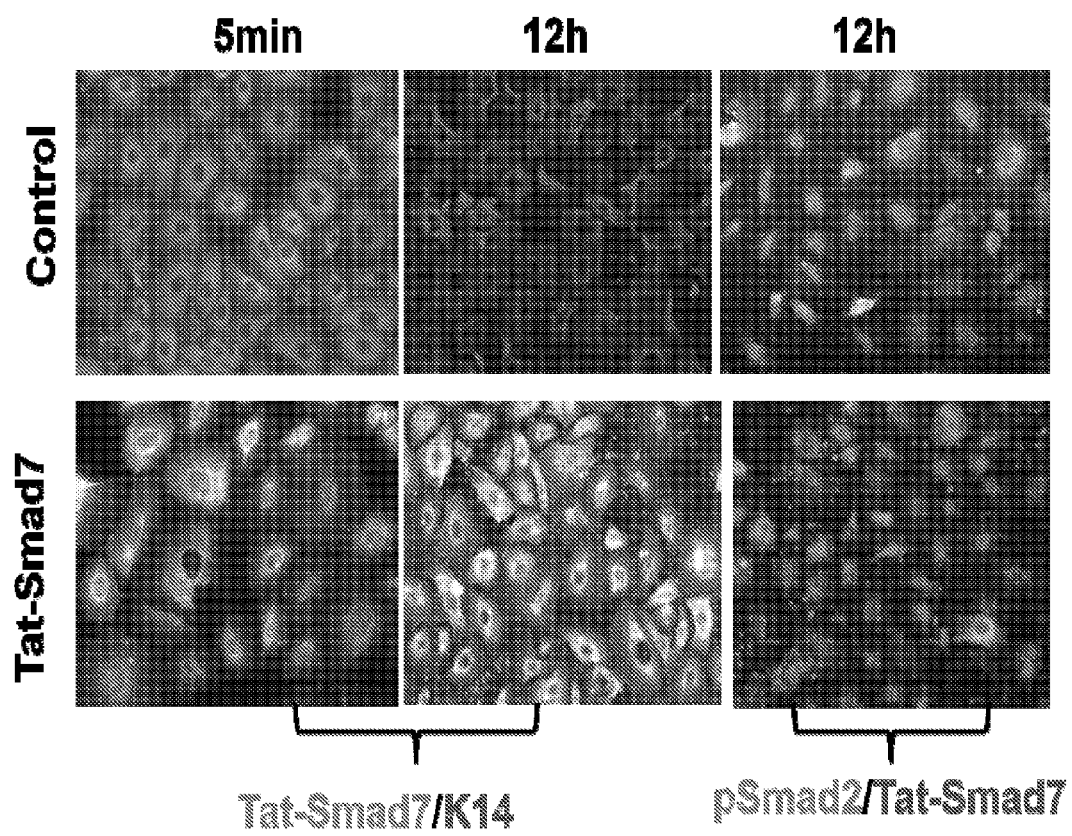
FIG. 3. Tat-Smad7 protein transduction to keratinocytes. Left and middle panels: Tat-Smad7 staining (green) in transduced cells, counterstained by a keratin K14 antibody (red). Right: pSmad2 (green) stains vehicle-treated (control) keratinocytes but not in Tat-Smad7 transduced cells. Tat-Smad7 staining using a V5 antibody showed nuclear and/or cytoplasmic staining of transduced cells but not in control cells.
Figure 4:
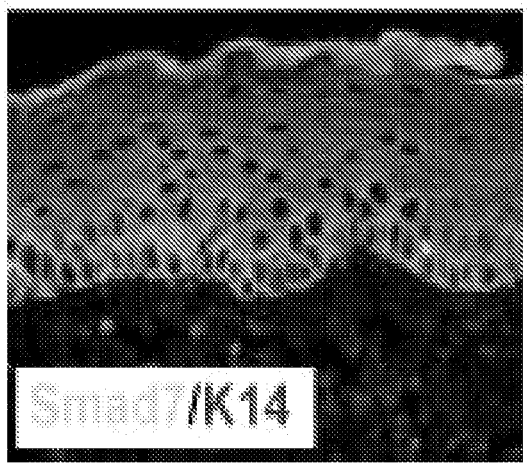
FIG. 4. Local Tat-Smad7 protein delivery to oral mucosa. Left: PBS buffer treated buccal mucosa. Right: buccal mucosa 24 h after oral Tat-Smad7 treatment. Tat-Smad7 was stained using a V5 antibody (counterstained by a K14 antibody).
Figure 4:
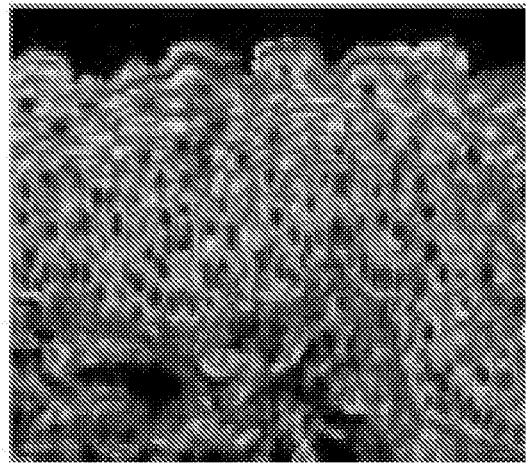

The inventors generated a recombinant human Smad7 (98% homology to mouse Smad7) with an N-terminal Tat-tag (Tat-Smad7) that allows proteins to permeate the cell membrane and reach the nucleus in a matter of seconds (Cardarelli et al., 2008; Kalvala et al., 2010; Brooks et al., 2005). The human Smad7 cDNA nucleotide sequence was altered to optimize codons for bacterial protein production and a 5' Tat-tag (9 aa) was added. The Tat.Smad7 was cloned into the pET101 protein expression vector (Invitrogen) for protein production in $E.\ coli$. The vector contains a V5 epitope for protein identification using a V5 antibody and 6×His tag for protein purification at the 3' of the Tat-Smad7 protein. The inventors tested purified Tat-Smad7 protein transduction at a concentration of 7.5 µg/ml. In less than 5 minutes after exposure to Tat-Smad7, nearly 100% of cells showed nuclear Tat-Smad7 (FIG. 3), which was retained at least the first 2 h after transduction. Later, Tat-Smad7 was also detected in the cytoplasm (FIG. 3), consistent with its ability to move between the nucleus and the cytoplasm (Zhang et al., 2007). In reference to previous reports that cytoplasmic Smad7 blocks TGFβ receptor-mediated Smad phosphorylation and/or increases Smad degradation (Massague et al., 2005), Tat-Smad7 transduced keratinocytes abrogated Smad2 phosphorylation (FIG. 3), suggesting it is functionally intact. Consistent with its long half-life, Tat-Smad7 was still detectable in cells 36 hr after withdrawal of the 5-min Tat-Smad7 treatment (not shown). To determine if this is rapid enough for Tat-Smad7 to penetrate oral mucosa in vivo, the inventors treated 5 mice orally with 10 µg of Tat-Smad7 in 10 µl phosphate buffered saline (PBS) buffer once, with an hour food/water restriction after treatment, and excised oral mucosa for Tat-Smad7 detection 24 h after treatment. Tat-Smad7 was detected uniformly in epithelial and stromal cells of oral mucosa (FIG. 4). These data suggest that local Tat-Smad7 delivery quickly achieves cellular uptake and should not require more than daily application.

Figure 5:
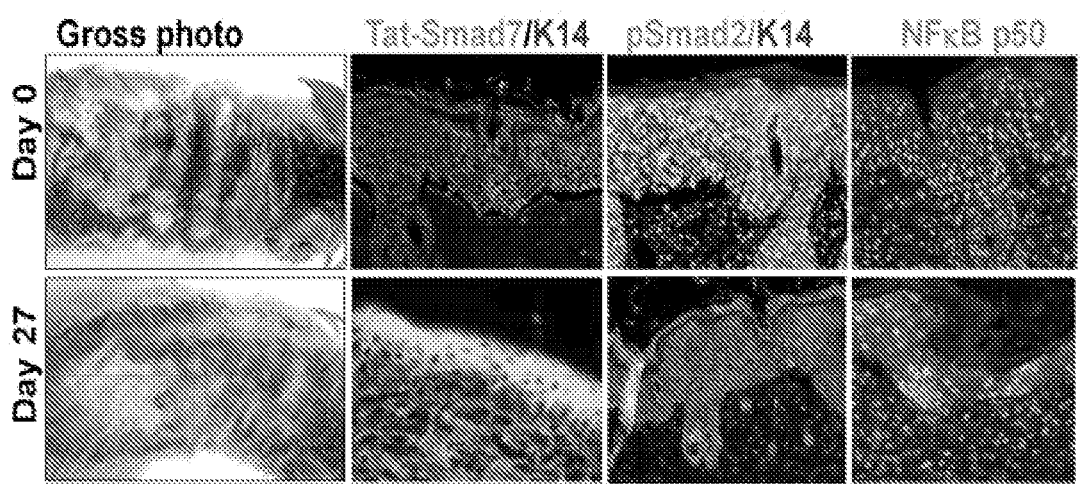
FIG. 5. Abrogation of skin inflammation by Tat-Smad7 protein. Upper: K5.TGFβ1 mouse gross photo and sections of his skin biopsy prior to treatment with thickened (wrinkled) skin and rash due to severe inflammation. Lower: the same mouse 27 days after treatment shows significant improvement with reduced pSmad2 and NFκB p50. Vehicle treated mice have no effects (not shown). Dotted lines highlight the epidermis.

Although the inventors have an endotoxin removal step in the purification process, they further assessed whether Tat-Smad7 is functional in vivo, and if potential endotoxin contamination from production in bacteria poses a toxicity risk. The inventors s.c.-injected Tat-Smad7 (10 µg/mouse, 3 times/wk) into K5.TGFβ1 mice which exhibit severe skin inflammation (Li et al., 2004). In all three, K5.TGFβ1 mice in this pilot experiment, Tat-Smad7 treatment significantly alleviated skin inflammation (FIG. 5) and no obvious side effects were observed. Immunofluorescence staining using a V5 antibody shows that s.c.-injected Tat-Smad7 protein accumulated in the dermis and throughout the epidermis (FIG. 5). Tat-Smad7-transduced K5.TGFβ1 skin showed reduced pSmad2 and NFκB p50 in both the epidermis and the stroma (FIG. 5).

Figure 6:
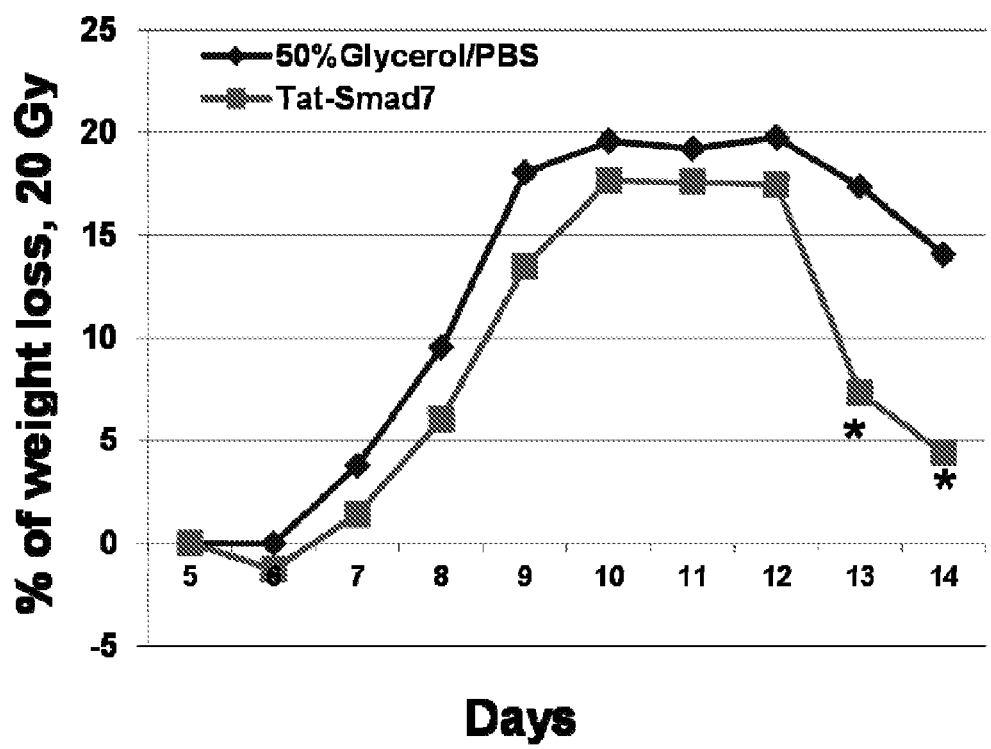
FIG. 6. Accelerated body weight recovery by orally treating Tat-Smad7 protein after 20Gy irradiation. Daily Tat-Smad7 treatment began on day 5 after radiation. Irradiation with 16Gy gives similar results (not shown). *: $p<0.05$.
Figure 7:
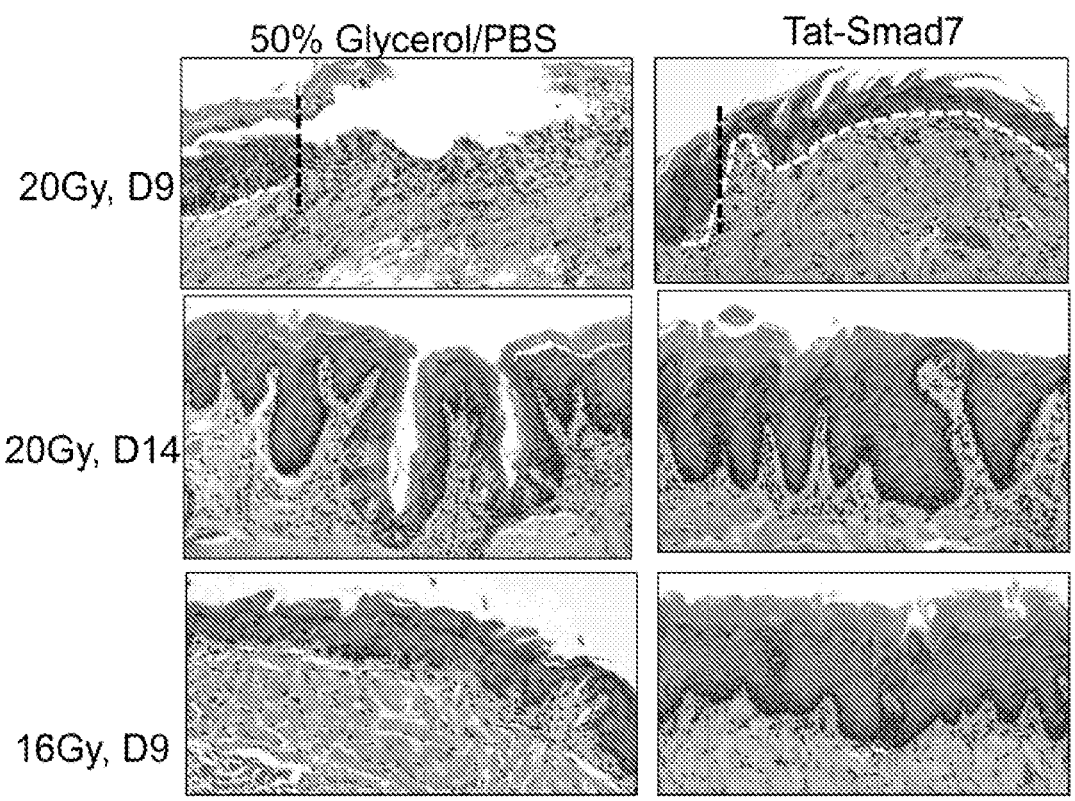
FIG. 7. Oral Tat-Smad7 treatment accelerated healing of oral mucositis. Black dotted lines on top panels highlight the center of damaged areas and white dotted lines highlight the epithelial-stromal boundary. Note oral mucosa treated with vehicle control developed oral mucositis with complete loss of epithelial layer on day 9 (D9) after 20Gy radiation whereas Tat-Smad7 treated mucosa retain thin layers of oral epithelium and numerous infiltrated leukocytes. By day 14, control mucosa has finished re-epithelialization with thin, undifferentiated epithelium and numerous leukocytes in the stroma, whereas Tat-Smad7 treated mucosa has almost completely recovered morphology and differentiation. Radiation with 16Gy induced oral epithelial thinning on day 9 in control mice but not in Tat-Smad7 treated oral epithelium.

To test if Tat-Smad7 can treat radiation-induced oral mucositis through oral delivery, the inventors irradiated mouse cranial facial area and treated mice with Tat-Smad7 afterwards. Seven-to-nine week old C3H female mice were anesthetized and exposed to 16Gy, 20Gy or 25Gy head irradiation with an RS2000 X-ray irradiator. Five days after irradiation, mice were treated daily with either 10 μg Tat.Smad7 dissolved in 50% glycerol/PBS or 50% glycerol/PBS (control), each group contained 4 mice, beginning on day 5 after irradiation when tissue damage in oral mucosa occurs. Grossly, Tat-Smad7 treated mice recovered body weight more rapidly than control mice with 16Gy or 20Gy irradiation (FIG. 6); control mice with 25Gy irradiation were all euthanized for humane reasons hence body weight recovery could not be monitored. Histology shows that by day 9 after 20Gy or 25Gy radiation, control mice developed oral mucositis (open ulcers, FIG. 7). In contrast, Tat-Smad7 treated mice had damaged oral mucosa with thinning epithelial layers but no ulcer formation (FIG. 7). Continual treatment of 20Gy irradiated mice with Tat-Smad7 till day 13 accelerated repair. By day 14, when oral mucositis ulcers just finished re-epithelialization in control mice, oral epithelia in Tat-Smad7 treated mice was almost completely recovered to normal morphology with only a few damaged epithelial cells and some infiltrated leukocytes (FIG. 7). With 16 Gy irradiation, tissue damage was most severe on day 9 in control mice with thinning and disorganized epithelial layers (FIG. 7), however, this dose of radiation is insufficient to cause oral mucositis and mice orally treated with Tat-Smad7 from day 5 to day 8 retained essentially normal epithelium (FIG. 7).

Figure 8:
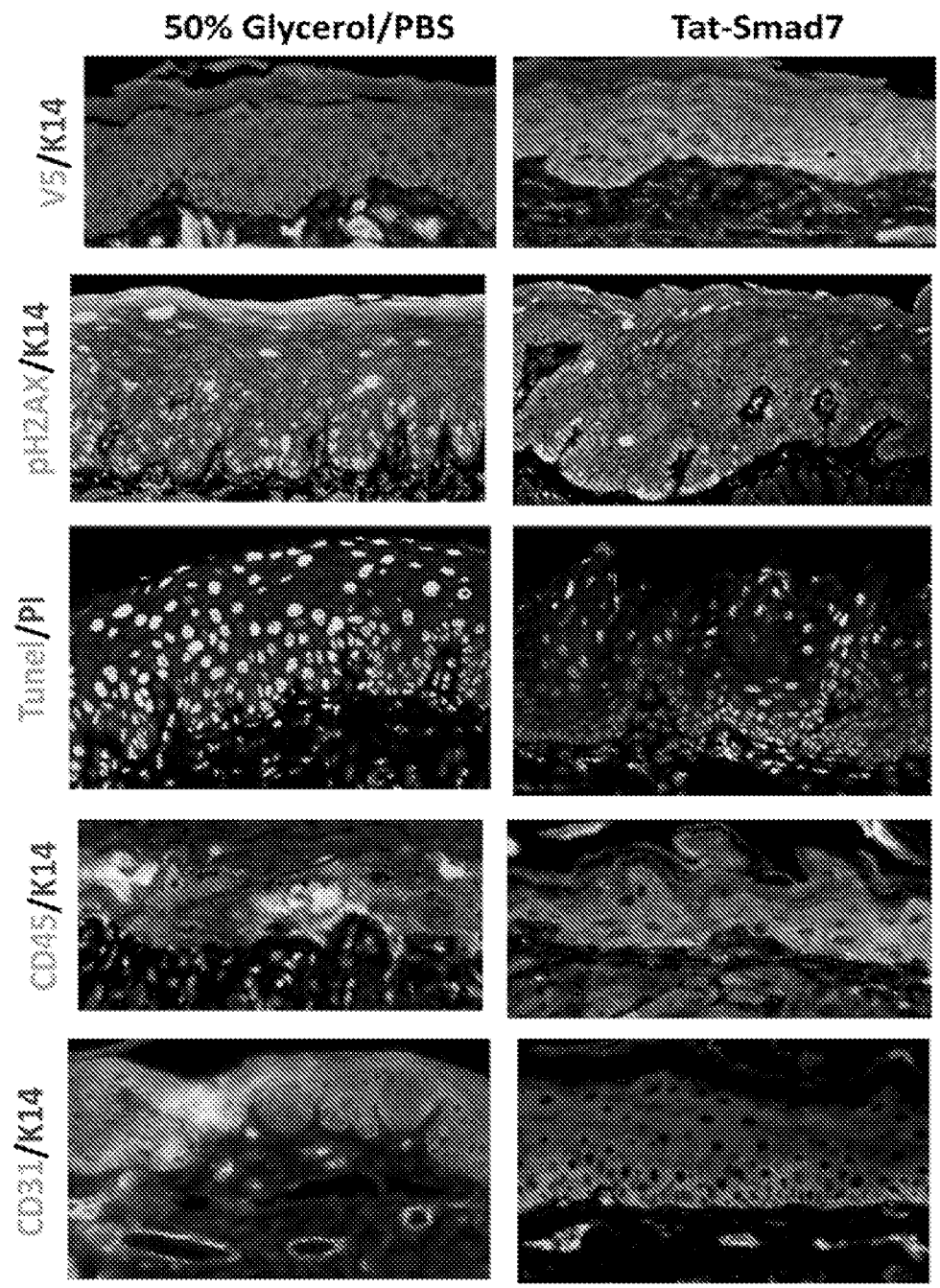
FIG. 8. Tat-Smad7 abrogates damage in radiation-induced oral mucositis. All sections are from oral mucosa immediately adjacent to the center of the damaged areas on day 14 after 20Gy irradiation, except CD45 staining, which are selected from the most damaged areas on day 9 after irradiation. K14 antibody was used to counterstain of epithelial layers except in Tunel assay.

Immunostaining using the antibody against the V5 tag of the Tat-Smad7 shows that Tat-Smad7 protein was delivered primarily to oral epithelial cells (FIG. 8). Cells positive for pH2AX, a DNA damage marker, were significantly reduced in Tat-Smad7-treated oral mucosa (FIG. 8). Consistent with observed DNA damage, apoptotic cells, as determined by TUNEL assay, were also significantly reduced in Tat-Smad7 treated oral mucosa (FIG. 8). Infiltrated leukocytes, identified by CD45 staining, were prominent in irradiated oral mucosa treated with vehicle control but were significantly reduced in Tat-Smad7 treated mucosa (FIG. 8). CD31 staining to highlight vessels, shows enlarged vessels in irradiated oral mucosa treated with vehicle control but normal vessel sizes in Tat-Smad7 treated oral mucosa (FIG. 8).

In sum, these data show that Tat-Smad7 local delivery can treat severe oral mucositis through preventing tissue damage, improving epithelial healing and reducing inflammation and vessel damage in the stroma.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

G. REFERENCES

The following references, to the extent that they provide exemplary procedural or other details supplementary to those set forth herein, are specifically incorporated herein by reference.

U.S. Pat. No. 4,684,611
U.S. Pat. No. 4,879,236
U.S. Pat. No. 4,952,500
U.S. Pat. No. 5,302,523
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,670,488
U.S. Pat. No. 5,702,932
U.S. Pat. No. 5,736,524
U.S. Pat. No. 5,780,448
U.S. Pat. No. 5,789,215
U.S. Pat. No. 5,871,986
U.S. Pat. No. 5,945,100
U.S. Pat. No. 5,981,274
U.S. Pat. No. 5,994,624
Ausubel et al., Curr. Protocols in Mol. Biol., Greene Pub. Assoc., Wiley Interscience, NY, 1994.
Brooks et al., Adv. Drug Deliv. Rev., 57(4): 559-577, 2005.
Cardarelli et al., Traffic., 9(4):528-539, 2008.
Chen and Okayama, Mol. Cell Biol., 7(8):2745-2752, 1987.
Fechheimer et al., Proc. Natl. Acad. Sci. USA, 84:8463-8467, 1987.
Fischer, Med. Res. Rev., 27(6):755-796, 2007.
Fraley et al., Proc. Natl. Acad. Sci. USA, 76:3348-3352, 1979.
Gopal, Mol. Cell Biol., 5:1188-1190, 1985.
Graham and Van Der Eb, Virology, 52:456-467, 1973.
Harland and Weintraub, J. Cell Biol., 101(3):1094-1099, 1985.
Imai et al., Nephrologie, 19(7):397-402, 1998.
Kaeppler et al., Plant Cell Rep., 9:415-418, 1990.
Kalvala et al., Nucleic Acids Res., 38(14):e149, 2010.
Kaneda et al., Science, 243:375-378, 1989.
Kato et al, J. Biol. Chem., 266:3361-3364, 1991.
Li et al., EMBO J., 23(8): 1770-1781, 2004.
Massague et al., Genes Dev., 19(23):2783-2810, 2005.
Nicolau and Sene, Biochim. Biophys. Acta, 721:185-190, 1982.
Nicolau et al., Methods Enzymol., 149:157-176, 1987.
Omirulleh et al., Plant Mol. Biol., 21(3):415-428, 1993.
PCT Appln. WO 94/09699
PCT Appln. WO 95/06128
Potrykus et al., Mol. Gen. Genet., 199(2):169-177, 1985.
Remington's Pharmaceutical Sciences, 15th Ed., 33:624-652, 1990.
Rippe, et al., Mol. Cell Biol., 10:689-695, 1990.
Robbins and Ghivizzani, Pharmacol Ther, 80(1):35-47, 1998.
Robbins et al., Trends Biotechnol., 16(1):35-40, 1998.
Sambrook & Russell, Molecular Cloning: A Laboratory Manual, Cold Spring Harbor Laboratory, NY, 1990.
Sambrook et al., In: Molecular cloning: a laboratory manual, $2^{nd}$ Ed., Cold Spring Harbor Laboratory Press, Cold Spring Harbor, N.Y., 1989.
Wong et al., Gene, 10:87-94, 1980.
Zhang et al., Mol. Cell Biol., 27(12):4488-4499, 2007.

What is claimed is:

1. A method for treating oral mucositis or psoriasis in a subject in need thereof comprising administering to the subject a therapeutically effective amount of a protein comprising Smad7 (mothers against decapentaplegic homolog 7) fused to a protein transduction domain (PTD), wherein the protein translocates to the nucleus.

2. The method of claim 1, wherein the protein comprising Smad7 is administered to the subject as a protein or is produced from an expression vector, wherein the expression vector expresses the protein within the subject.

3. The method of claim 1, wherein the protein comprising Smad7 further comprises a regulatory domain that prevents Smad7 function in the absence of an activator, the method further comprising providing the activator.

4. The method of claim 1, wherein the protein comprising Smad7 is administered in a formulation on a patch, in a gelatinous composition, in a microsphere, in a microbead or combination thereof.

5. The method of claim 1, wherein the protein comprising Smad7 is administered locally to an affected region.

6. The method of claim 1, wherein the protein comprising Smad7 is administered systemically.

7. The method of claim 1, further comprising administering a second anti-inflammatory therapy to said subject.

8. The method of claim 1, wherein the PTD is Tat.

9. The method of claim 1, wherein the protein comprising Smad7 further comprises a detectable marker.

10. The method of claim 1, wherein the subject has oral mucositis.

11. The method of claim 10, further comprising administering a second mucositis therapy to said subject.

12. The method of claim 11, wherein said second mucositis therapy is viscous 2% lidocaine, baking soda solution, saline solution, BAX solution, beta carotene, tocopherol, laser irradiation, silver-nitrate, misoprostol, leucovorin, systemic keratinocyte growth factor, pentoxifylline, allopurinol, systemic sucralfate, chlorhexidine gluconate or cryotherapy.

13. The method of claim 10, wherein the subject comprises a subject having a transplant, a subject having cancer or a subject having a condition requiring radiation therapy.

14. The method of claim 13, wherein the subject has cancer and the cancer is selected from the group consisting of oral cancer, colon cancer, breast cancer, head and neck cancer, pancreatic cancer and other cancers treated with upper body radiation or repeated cycles of chemotherapy.

15. The method of claim 10, wherein the subject has undergone upper-body radiation.

16. The method of claim 1, further comprising administering the protein comprising Smad7 to the subject a second time.

17. The method of claim 1, wherein the subject has psoriasis.

18. The method of claim 1, wherein the protein comprising Smad7 is formulated with one or more pharmaceutically acceptable excipients.

19. The method of claim 18, wherein the one or more pharmaceutically acceptable excipients is selected for topical administration.

20. The method of claim 18, wherein the one or more pharmaceutically acceptable excipients is selected for systemic administration.

* * * * *

UNITED STATES PATENT AND TRADEMARK OFFICE
CERTIFICATE OF CORRECTION

PATENT NO. : 9,084,746 B2
APPLICATION NO. : 13/822173
DATED : July 21, 2015
INVENTOR(S) : Xiao-Jing Wang et al.

Page 1 of 1

It is certified that error appears in the above-identified patent and that said Letters Patent is hereby corrected as shown below:

In the specification, column 1, line 13 "GM70966" should be changed to --GM070966-- and "Institute" should be changed to --Institutes--.

Signed and Sealed this
Third Day of November, 2015

Michelle K. Lee
*Director of the United States Patent and Trademark Office*